United States Patent
Tian et al.

(10) Patent No.: US 12,364,671 B1
(45) Date of Patent: Jul. 22, 2025

(54) METHODS OF ADMINISTERING VITAMIN A AND LACTIC ACID TO GILTS

(71) Applicant: CHINA AGRICULTURAL UNIVERSITY, Beijing (CN)

(72) Inventors: Jianhui Tian, Beijing (CN); Shumin Wang, Beijing (CN); Lei An, Beijing (CN); Guo Sun, Beijing (CN); Fupeng Wang, Beijing (CN); Qianying Yang, Beijing (CN)

(73) Assignee: CHINA AGRICULTURAL UNIVERSITY, Beijing (CN)

( * ) Notice: Subject to any disclaimer, the term of this patent is extended or adjusted under 35 U.S.C. 154(b) by 0 days.

(21) Appl. No.: 18/955,996

(22) Filed: Nov. 22, 2024

(30) Foreign Application Priority Data

Apr. 7, 2024 (CN) .......................... 202410408237.7

(51) Int. Cl.
| | | |
|---|---|---|
| A61K 31/07 | (2006.01) | |
| A61D 17/00 | (2006.01) | |
| A61D 19/02 | (2006.01) | |
| A61K 9/00 | (2006.01) | |
| A61K 31/19 | (2006.01) | |
| A61K 38/24 | (2006.01) | |
| A61P 15/08 | (2006.01) | |

(52) U.S. Cl.
CPC ............ A61K 31/07 (2013.01); A61D 17/002 (2013.01); A61D 19/02 (2013.01); A61K 9/0056 (2013.01); A61K 31/19 (2013.01); A61K 38/24 (2013.01); A61P 15/08 (2018.01)

(58) Field of Classification Search
None
See application file for complete search history.

(56) References Cited

U.S. PATENT DOCUMENTS

| 6,028,057 | A | 2/2000 | Burns |
| 2002/0028849 | A1* | 3/2002 | Godkin .................. A61K 31/07 800/21 |
| 2015/0306169 | A1 | 10/2015 | Webel et al. |
| 2020/0375980 | A1 | 12/2020 | Bertaim et al. |

FOREIGN PATENT DOCUMENTS

| CN | 103609888 A | 3/2014 |
| CN | 104161210 A | 11/2014 |
| CN | 104814280 A | 8/2015 |
| CN | 105409871 A | 3/2016 |
| CN | 106456704 A | 2/2017 |
| CN | 113398243 A | 9/2021 |
| CN | 116439198 A | 7/2023 |
| CN | 116806775 A | 9/2023 |
| RU | 2011127038 A | 1/2013 |
| RU | 0002785290 C1 | 12/2022 |
| RU | 0002795159 C1 | 4/2023 |
| SU | 1625469 A1 | 2/1991 |

OTHER PUBLICATIONS

Partanen et al., Agricultural and Food Science, 15 (2006): 324-339 (Year: 2006).*
Wähner et al., Reprod Dom Anim (1996) 31, 477-482 (Year: 1996).*
First Office Action from corresponding Chinese Application No. 202410408237.7, dated May 9, 2024. English translation attached.
The Grant Notice from corresponding Chinese Application No. 202410408237.7, dated Jun. 3, 2024. English translation attached.
First Search from corresponding Chinese Application No. 202410408237.7, dated May 9, 2024. English translation attached.

* cited by examiner

*Primary Examiner* — Christina M Borgeest

(57) ABSTRACT

The present disclosure relates to the field of livestock farming, and specifically provides a feeding method for gilts in batch for promoting onset of puberty and alleviating estrus disorder of gilts, which is aiming at an industrial problem that a large number of gilts are culled due to delayed puberty onset or estrus disorder. The method includes: feeding, prior to onset of puberty for gilts with vitamin A combined with lactic acid; and performing, subsequent to the puberty onset of gilts, estrus synchronization treatment and insemination treatment on the gilts. By applying vitamin A combined with lactic acid, the present disclosure alleviates the delayed puberty onset or estrus disorder of the gilts, reduces the feeding duration and feeding cost of the gilts, facilitates synchronous estrus treatment of the gilts.

19 Claims, 6 Drawing Sheets

METHODS OF ADMINISTERING VITAMIN A AND LACTIC ACID TO GILTS

CROSS-REFERENCE TO RELATED APPLICATION

This application claims priority to Chinese Patent Application No. 202410408237.7 filed on Apr. 7, 2024, the entire disclosure of which is incorporated herein by reference.

TECHNICAL FIELD

The present disclosure relates to the field of livestock farming, and specifically provides a batch breeding method for promoting puberty onset and alleviating estrus disorder of gilts.

BACKGROUND

A batch farrowing is to formed pigs into groups which allow for estrus, mating and farrowing to occur within the same period by utilizing biotechnology. It is an efficient and controllable management system for improving the economic benefits of sow batch production. Compared with a traditional continuous-flow system, the batch farrowing can really lead to an all-in-all-out management of pigs, which achieve efficient cleansing and disinfection, break the chain of infection and prevent disease buildup. By accurately controlling the reproductive cycle of the sow, the batch farrowing makes better production schedule, reduces non-productive days of the sows and results in high reproductive efficiency of sows. In addition, it is a strategy for improving the growth rates and feed efficiency of the growing and finishing herd. Today, the batch farrowing has been widely practiced in multiple countries, using for improving quality and efficiency and upgrading technology of swine industry.

The estrous synchronization of gilts can be achieved by feeding hormones like altrenogest in batch farrowing management. Now, gilts have low estrus rates, which can significantly impact reproductive performance and overall herd productivity. The gilts are prone to estrus abnormally such as delayed puberty, latent estrus, anestrus, and delayed estrus, which leads to the reproductive problems of longer feeding duration before housed in batch herd and lower estrus rate, thereby severely affecting the reproductive efficiency of the gilts. To improve onset of puberty, gilts at 150-160 d of age are received daily boar exposure and boar pheromone for estrus testing. After selecting and training, gilts exhibiting puberty are fed with altrenogest at 150-160 d of age to synchronize estrus cycle. If the gilts are without puberty at 190 d of age, pregnant mare serum gonadotropin (PMSG) or P.G. 600 (contains 400 IU PMSG and 200 IU hCG) is injected, and injected again with the gilts showing no estrus at 204 d of age. Then expression of estrus is also recorded. Finally, gilts that failed to estrus are culled. Nevertheless, using PMSG for gilts or sows in batch farrowing comprise many disadvantages, such as (1) the PMSG is a pregnancy hormone found in the blood of mares, which is produced from the chorion (fetal membrane), and is also called equine chorionic gonadotropin (eCG). Non-governmental organizations in European repeatedly call on the Commission and Member States to stop the import and domestic production of PMSG because of the production process involving animal health- and welfare issues. The using of PMSG will also face great risks in the future. (2) The PMSG injection is only a supplementary way for onset of puberty in gilts, and it has no idea about the precision dose for gilts response to PMSG; and a massive overdose of PMSG may cause ovarian hyperstimulation. (3) It is also not good for dividing gilts in batch quickly when PMSG is injected too late. (4) The cost of using PMSG in gilts or sows is higher. Although the gilts may be stimulated to estrus by means with boar exposure and hormone treatment, the effect is not stable. Therefore, it is urgent to develop a more safe and effective method for promoting puberty onset and estrus in gilts.

Therefore, up to now, batch farrowing of the gilts still needs further in-depth study.

In the early 20th century, for the first time, people realized the requirement on vitamin A in animal reproduction and development process, including processes such as formation of reproductive cells and embryo development. For example, the estrus of gilts will be delayed because of lacking vitamin A; and it may also lead to abortion during mid-pregnancy even if breeding and conception is conducted after estrus. Due to a close relationship between the vitamin A and animal reproduction, the vitamin A has been repeatedly used in study of controlling livestock reproduction. Some studies have found that, the lambing rate of sheep fed with vitamin A (50000 IU per day, continuously fed by 50 days) can be significantly increased, but an estrus rate has no significantly affected. However, both the estrogen level and the conception rate can be significantly increased in cows with reproductive disorders, which are fed with R carotene (200 mg per day)+vitamin A (50000 IU per day) or the vitamin A (50000 IU per day) alone, but the follicle size and estrus ate are not significantly affected.

SUMMARY

The present disclosure aims at solving the technical problems existing in the prior art to some extent at least. In view of this, the present disclosure provides a method for gilts housed in batch farrowing to alleviate the delayed puberty onset or estrus disorder by applying vitamin A combined with lactic acid, and also can reduce the feeding duration and feeding cost, facilitate synchronous estrus treatment, increase an estrus rate, and significantly increase a piglet index of the gilts. The method has great values of promoting batch farrowing used in pig farms, achieving the goal of "all-in-all-out", reducing costs and increase efficiency in pig industry.

It should be noted that, the present disclosure is provided based on the inventor's discovery and understanding of the facts and problems as follows.

According to provisions of Academician Li Defa, et al. in *Nutrient Requirements of Swine in China and Nutrient Requirements of Swine*, a vitamin A requirement of lean gilts is 5000 IU/kg, while that of fatty gilts is 1700 IU/kg. In contrast, the US National Research Council (NRC) stipulates that, the vitamin A requirement of gilts is 1300 IU/kg. However, it is found by the inventors through experiments that, even if the gilts are fed with daily ration that meets the above vitamin A requirement, it is still difficult to effectively alleviate the problems of delayed puberty onset or estrus disorder of the gilts. Thus, it is indicated that reproductive performance of the gilts may be affected by other factors, and these problems cannot be solved by providing enough vitamin A alone. Therefore, it still needs to further research and explore other possible nutritional or environmental factors so as to better improve the reproductive performance of the gilts.

Based on the above discovery, the inventors tried to feed extra vitamin A, in addition to the diet, to gilts prior to their estrus initiation and found that this could improve the delayed estrus initiation or estrus disorder in gilts to some extent. Further, after in-depth investigation, the inventors found that, the protein expression of lactate dehydrogenase A (LDHA), a key enzyme for lactic acid synthesis, was significantly increased in mice during estrus initiation (FIG. 1). Therefore, the inventors speculated that the lactic acid may be beneficial to the puberty onset and estrus of the gilts. To verify such a speculation, the inventors tried to feed the gilts with combination of vitamin A and lactic acid before the puberty onset, and were surprised to find that the puberty onset and estrus disorder of the gilts can be significantly alleviated.

For this purpose, in one aspect of the present disclosure, the present disclosure provides a batch breeding method for gilts. According to embodiments of the present disclosure, the method includes: feeding, prior to puberty onset, the gilts with vitamin A combined with lactic acid; and performing, subsequent to the puberty onset, estrus synchronization treatment and insemination treatment on the gilts.

According to the method in the embodiments of the present disclosure, by feeding the gilts with vitamin A combined with lactic acid, the delayed puberty onset or estrus disorder of the gilts can be alleviated. Particularly, a state of low estrogen synthesis of gilts or sows having latent estrus and anestrus can be alleviated, thereby further solving problems of high culling ratio of the gilts and increased feeding duration before moved in batch herd due to the latent estrus, anestrus and other estrus disorders. This method can improve the reproductive efficiency, and increase an estrus rate and a piglet index, thereby decreasing the feeding duration and feeding cost of the gilts. The implementation of the method facilitates estrus synchronization treatment of the gilts, thus promoting batch farrowing used in pig farm, and achieving a goal of "all-in-all-out" in batch farrowing target of pig farming. In addition, the method further facilitates to reduce costs and increase efficiency in pig industry, and increases production efficiency and economic benefits, and has great value and significance on the development of whole pig industry.

According to the embodiments of the present disclosure, the batch breeding method for the gilts can also have additional technical features as follows.

According to the embodiments of the present disclosure, for each gilt, a feeding amount of the vitamin A ranges from 5,000 IU to 50,000 IU per day, and a feeding amount of the lactic acid ranges from 0.3 g to 5 g per day; and the vitamin A combined with lactic acid is provided in the form of a mixture containing vitamin A, lactic acid and oil.

According to the embodiments of the present disclosure, the gilts are fed with the vitamin A combined with lactic acid every day from an age of 130 d to 150 d until the puberty onset or until the estrus synchronization treatment is performed on the gilts.

According to the embodiments of the present disclosure, the step of feeding the gilts with the combination of vitamin A and lactic acid further includes: the gilts are fed in small group for 8-15 days; then fed in breeding unit pens for 20-50 days until the puberty onset or until the estrus synchronization treatment is performed on the gilts, wherein a daily ration adopted for gilts during housed in small-group contains vitamin A at a concentration of 1,600 IU/kg to 1,800 IU/kg and contains no lactic acid; and a daily ration adopted for gilts during housed in breeding unit pen contains the vitamin A at a concentration of 4,600 IU/kg to 4,800 IU/kg and contains no lactic acid.

According to the embodiments of the present disclosure, prior to feeding the gilts with vitamin A combined with lactic acid, the method further includes: performing a feed induction treatment on the gilts in advance, wherein: a time of the feed induction treatment is 2-4 days; and the feed induction treatment includes an attractant is fed twice daily, one in the morning and one in the afternoon.

According to the embodiments of the present disclosure, the step of feeding the gilts with vitamin A combined with lactic acid is performed in the afternoon every day; and the time of feeding vitamin A combined with lactic acid is consistent with that of feed induction.

According to the embodiments of the present disclosure, the estrus synchronization treatment includes feeding the gilts with 15 mg to 25 mg of altrenogest for 15-20 days per day; subsequent to the completion of the estrus synchronization treatment, timed-artificial insemination treatment or fixed-time artificial insemination treatment are performed on the gilts; the timed-artificial insemination treatment includes: performing estrus detection on the gilts, and performing insemination on the gilts subsequent to the appearance of estrus representation; the fixed-time artificial insemination treatment includes: applying exogenous gonadotropins and promoting ovulation induction to the gilts for facilitating synchronization of follicular development and ovulation; and performing timed insemination on the gilts.

In another aspect of the present disclosure, the present disclosure provides a batch breeding method for gilts. According to the embodiments of the present disclosure, the method includes:

feeding gilts with vitamin A combined with lactic acid from 140 d of age until estrus synchronization treatment is performed, a total of the vitamin A ranging from 5,000 IU to 50,000 IU per day, and the total of the lactic acid ranging from 0.3 g to 5 g per day, wherein the gilts firstly housed in small-group are fed for 10 days and then transferred to breeding unit pen for continuously feeding till an age of 209 d. A daily ration fed for gilts in small-group contains vitamin A at a concentration of 1,700 IU/kg, and that fed in breeding unit pen contains vitamin A at a concentration of 4700 IU/kg. The gilts in small-group are fed ad libitum, and an average daily feed intake of gilts in breeding unit pen is 2.2 kg per day; feeding, the pubertal gilts from an age of 210 d with altrenogest for 18 consecutive days to synchronize estrus, wherein the altrenogest is fed by 20 mg per day;

performing, from the second day following the end of altrenogest, an estrus detection on the gilts every day;

performing, subsequent to the appearance of estrus sign, first insemination at an interval of 8-16 hours; and performing second insemination at an interval of 24 hours later.

In another aspect of the present disclosure, the present disclosure provides an application of vitamin A combined with lactic acid in preparation of pig feed. According to the embodiments of the present disclosure, the feed is used for at least one of the following: feeding the gilts housed in batch farrowing; promoting puberty onset of the gilts; increasing an estrus rate and a piglet index of the gilts; alleviating estrus disorder of the gilts; shortening feeding duration of the gilts before entering the batch herd; and promoting estrogen synthesis of the gilts.

According to the embodiments of the present disclosure, the estrus disorder includes latent estrus or anestrus; and the feed is used for facilitating the expression of Cyp19a1 gene in follicular granulosa cells.

Additional aspects and advantages of the present disclosure will be given in descriptions below. Some of the aspects and advantages will be obvious from the descriptions below, or will be understood through practice of the present disclosure.

BRIEF DESCRIPTION OF DRAWINGS

The above and/or additional aspects and advantages of the present disclosure will be obviously and easily understood from descriptions of embodiments in combination with figures below, in which:

FIG. 2B, treatment of the granular cells in mice with vitamin A combined with lactic acid promotes the protein expression of a key enzyme CYP19A1 in estrogen synthesis in the granular cells of mice; and FIG. 2C, treatment of the granular cells in mice with vitamin A combined with lactic acid promotes synthesis of estradiol in the granular cells of mice;

DESCRIPTION OF EMBODIMENTS

Figure 1:
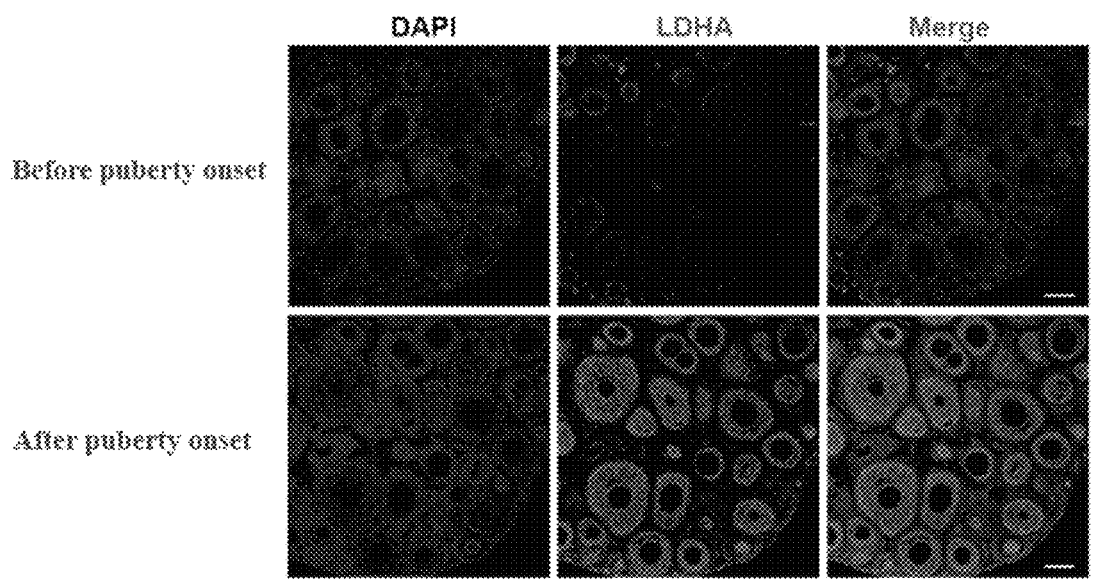
FIG. 1 shows an expression analysis diagram (immunofluorescence staining analysis) of a key enzyme LDHA for lactic acid synthesis in ovaries of pre-pubertal mice and post-pubertal mice.

Embodiments of the present disclosure will be described in detail below. The embodiments described below are illustrative, are merely used for explaining the present disclosure, but cannot be understood as a limitation to the present disclosure.

It should be noted that, unless otherwise specified, in the descriptions of the present disclosure, "multiple" means two or more. The endpoints of ranges and any values disclosed herein are not limited to the accurate range or value, and these ranges or values should be understood to include values close to these ranges or values. For numerical ranges, the endpoint values of the various ranges, the endpoint values and the individual point values of various ranges, and the individual point values may be combined with one another to obtain one or more new numerical ranges. These numerical ranges should be regarded as specifically disclosed herein.

Herein, the term "include" or "comprise" is an open expression, namely including the content specified in the present disclosure, but shall not exclusive the contents in other aspects.

The present disclosure provides a feeding method for gilts in batch farrowing and a use of vitamin A combined with lactic acid in the sow feed. The method and the use are respectively described in detail below.

Batch Farrowing for Gilts

In one aspect of the present disclosure, the present disclosure provides a feeding method for gilts in batch farrowing. According to embodiments of the present disclosure, the method includes: feeding, before the onset of puberty, the gilts with vitamin A combined with lactic acid; and performing, subsequent to the onset of puberty, estrus synchronization and insemination treatment on the gilts. Specifically, it includes feeding the gilts with vitamin A combined with lactic acid until the puberty onset, or until the estrus synchronization treatment is performed, that is, when the estrus synchronization treatment is started, the feeding of vitamin A combined with lactic acid is stopped.

It should be noted that, the feeding method for gilts in batch farrowing in the present disclosure is used for a non-disease treatment purpose.

Unless otherwise specified, the term "gilts" used herein refers to female pigs that have had no more than one litter, which have moderate age, good health and sexual maturation but have not been subjected to first mating, and generally refers to gilts that are reserved as breeding pigs until the piglets are matured to the first mating. The gilts are prone to have estrus disorders such as delayed puberty onset, latent estrus or anestrus; and all the estrus disorders are closely related to low estrogen levels of the gilts. Due to the climatic environment and other factors, the delayed puberty onset or estrus disorder in gilts is more obvious.

As mentioned above, according to the embodiments of the present disclosure, before the onset of puberty, the gilts are additionally fed with vitamin A combined with lactic acid in addition to the daily ration, so that the delayed puberty onset or estrus disorder (latent estrus or anestrus) of the gilts can be effectively alleviated, thereby increasing the reproduction efficiency, estrus rate and the piglet index of the gilts, and shortening the feeding duration before fed in batch herd.

Under the natural state, the individual physiological cycles of gilts are different; the gilts can be fed with altrenogest to synchronize estrus after the onset of puberty, which is helpful to promote rapidly gilts moved into the batch herd, increase the reproduction efficiency of the gilts, decrease a culling ratio of the gilts, and increase farrowing efficiency of each batch.

According to the embodiments of the present disclosure, for each gilt, a feeding amount of vitamin A ranges from 5000 IU/d to 50000 IU/d, and the feeding amount of lactic acid ranges from 0.3 g/d to 5 g/d. In some embodiments, for each gilt, the feeding amount of vitamin A is 5000 IU/d, 10000 IU/d, 20000 IU/d, 30000 IU/d, 40000 IU/d, 50000 IU/d, or a range value formed by taking any two values as endpoint values, preferably 10000 IU/d to 40000 IU/d, more preferably 20000 IU/d to 30000 IU/d. The feeding amount of lactic acid is 0.3 g/d, 0.6 g/d, 1.0 g/d, 2.0 g/d, 3.0 g/d, 4.0 g/d, 5.0 g/d or a range value formed by taking any two values as endpoint values, preferably 0.6 g/d to 3.0 g/d, more preferably 1.0 g/d to 2.0 g/d. Through a series of experimental studies, it is concluded that, with the adoption of the above feeding amount, the puberty onset of the gilts can be effectively advanced or the estrus disorder can be alleviated, thereby increasing the reproductive efficiency, estrus rate and the piglet index of the gilts, and shortening the feeding duration before transferred to bath herd.

According to the embodiments of the present disclosure, the vitamin A in the mixture can be vitamin A palmitate; and the lactic acid can be a lactic acid preparation with purity more than 98%. According to the embodiments of the present disclosure, the vitamin A combined with lactic acid is provided in the form of a mixture containing vitamin A, lactic acid and oil. Thus, it is convenient for vitamin A to dissolve therein. In some embodiments, the oil is selected from oil that can be served as pig feed, including but not limited to soybean oil, corn oil and peanut oil. Therefore, it is more convenient for the gilts to intake the vitamin A and lactic acid; and the reproductive efficiency of gilts in batch farrowing is further increased.

According to the embodiments of the present disclosure, the gilts are fed with vitamin A combined with lactic acid every day from an age of 130 d to 150 d until the puberty onset or until the estrus synchronization treatment is performed.

As mentioned above, the gilts have great individual differences, many gilts are in a state of low estrogen level under the natural state, which is characterized by delayed puberty onset or estrus disorder. By feeding the vitamin A combined with the lactic acid, the puberty onset can be effectively advanced or the estrus disorder can be alleviated, thereby increasing estrus rate, which in turn increase the reproductive efficiency and piglet index of the gilts, and shortening the feeding duration before moved into batch herd.

According to the embodiments of the present disclosure, feeding procedures include: performing feeding (ad libitum) on the gilts firstly in small groups; and then performing feeding in breeding unit pen. This feeding method meets the feeding rules of the gilts in batch farrowing in pig farms.

Herein, the term "fed in small group" refers to a method for dividing the gilts into small groups and performing feeding ad libitum management according to characteristics and needs of each small group. This is beneficial to manage the feeding process of the pig herds effectively, so as to meet feeding requirements of pigs at different development stages and growth rates, thereby increasing growth efficiency and health levels of the pig herds. In some embodiments, the number of gilts in each small-group is 14 to 25; and the ad libitum is adopted.

Herein, the term "fed in breeding unit pen" refers to feeding the pigs alone or in groups by arranging special fences or feeding troughs in the pigsty. According to such a way, a farmer may divide the pig herds into different groups according to characteristics such as weight, variety and growth stages, and provide relatively fixed feed and feeding patterns for each group. In some embodiments, each breeding unit pen is used for feeding one pig.

According to the embodiments of the present disclosure, the feeding duration of gilts in small-group (ad libitum) is 8 to 15 days, and that in breeding unit pen is 20 to 50 days. In some embodiments, the feeding duration in small-group is 8 days, 9 days, 10 days, 11 days, 12 days, 15 days, or a range value formed by taking any two values as endpoint values; and the feeding duration in breeding unit pen is 20 days, 25 days, 30 days, 35 days, 40 days, 45 days, 50 days, or a range value formed by taking any two values as endpoint values. When the gilts in breeding unit pen do not show initial estrus at 200 d of age, feeding of the vitamin A combined with the lactic acid and the subsequent treatment is stopped.

According to the embodiments of the present disclosure, a daily ration adopted during fed in the small-group contains vitamin A at a concentration of 1,600 IU/kg to 1,800 IU/kg and contains no lactic acid; and a daily ration adopted during fed in breeding unit pen contains vitamin A at a concentration of 4,600 IU/kg to 4,800 IU/kg and contains no lactic acid. In some embodiments, the concentration of vitamin A for feeding the gilts in small-group is 1600 IU/kg, 1650 IU/kg, 1700 IU/kg, 1750 IU/kg, 1800 IU/kg, or a range value formed by taking any two values as endpoint values; and the concentration of vitamin A for feeding the gilts in breeding unit pen is 4600 IU/kg, 4650 IU/kg, 4700 IU/kg, 4750 IU/kg, 4800 IU/kg, or a range value formed by taking any two values as endpoint values. However, the daily ration contains no lactic acid.

It should be noted that, an appropriate amount of the vitamin A may be added into the daily ration according to related standards to meet the daily growth requirements of the gilts. However, it is difficult to solve the problem of delayed puberty onset or estrus disorder for the gilts by taking the vitamin A in the daily ration. Through experiments, the inventors of the present disclosure were surprised to find that, supplementing vitamin A combined with lactic acid prior to the puberty onset can effectively advance the puberty onset of the gilts, and alleviate the problems of estrus disorder and so on.

According to the embodiments of the present disclosure, prior to fed with the vitamin A combined with the lactic acid, the gilts are treated with attractant. Thus, it is convenient for the gilts to better accept the combination of vitamin A and lactic acid.

According to the embodiments of the present disclosure, the duration of using attractant is 2 to 4 days (e.g., 2 days, 3 days, 4 days or a range value formed by taking any two values as endpoint values); and the attractant are fed twice daily, one in the morning and one in the afternoon. Therefore, it can further make the gilts to better accept the combination of vitamin A and lactic acid. The attractant, a feed flavoring agent or a feed flavoring matter, which belongs to non-nutritive additives, is an additive added into the feed to improve feed palatability and attraction, and then increase the feed quality and the feed conversion ratio. The attractant is mainly prepared from natural volatility substances (such as concentrate extracted from roots, stems, leaves, flowers and fruits of plants) and synthetic flavor materials (such as aldehydes, ketones, alcohols, acids, esters, ethers and other compounds). Generally, the attractant can make the sows get a pleasant appetite psychology, which is transmitted to the digestive system through conditioned reflex, thereby facilitating massive secretion of saliva, gastric juice, pancreatic juice and bile. Thus, secretion of amylase, protease and lipase are increased, gastrointestinal peristalsis is accelerated, and it is benefit for digestion and absorption capacity of feed for animals, thereby facilitating growth and development of animals, increasing production performance of the animals and feed utilization efficiency.

According to the embodiments of the present disclosure, the step of feeding the gilts with vitamin A combined with lactic acid is performed in the afternoon every day; and the feeding time is consistent with that of attractant. According to the embodiments of the present application, by using this mean, gilts can better intake the vitamin A combined with lactic acid, probably because the gastrointestinal tracts of the gilts are in a better absorption state and the gilts have better appetite at this time and easily accept the feeding. By ensuring that the feeding time is consistent with that of treatment, it can also improve the acceptance of feed for gilts, so as to realize the regulation of estrus more effectively and improve production efficiency.

According to the embodiments of the present disclosure, the estrus synchronization includes the gilts are fed 15 to 25 mg of altrenogest per day (such as, 15 mg/day, 18 mg/day, 20 mg/day, 22 mg/day, 25 mg/day, or a range value formed by taking any two values as endpoint values) for 15 to 20 days (15 days, 16 days, 17 days, 18 days, 19 days, 20 days, or a range value formed by taking any two values as endpoint values).

According to the embodiments of the present disclosure, after estrus synchronization, timed-artificial insemination treatment or fixed-time artificial insemination treatment are performed on the gilts.

In some embodiments, the timed-artificial insemination treatment includes: estrus is detected, and insemination is done on the gilts after the appearance of estrus representation. The estrus detection on the gilts is performed every day; and when standing heat occurs, it shows that the gilts are in estrus. Then, the gilts are artificially inseminated firstly at 8-16 h after first detecting estrus, the second insemination is performed 24 h later.

In some embodiments, the fixed-time artificial insemination treatment includes: gilts are synchronized follicular development and ovulation by applying exogenous gonadotropins and ovulation induction, and then performed fixed-time insemination. The exogenous gonadotropins and ovulation induction are applied to the gilts (e.g., PMSG is injected at 42 h after the end of altrenogest, followed 80 h later by injecting GnRH). And then, the gilts are artificially inseminated firstly at 24 h after injecting GnRH, the second insemination is performed 16 h or 24 h later.

In addition, the present disclosure provides another batch-rearing method for gilts. The method includes: when the gilts reach the age of 140 d, they are fed with vitamin A combined with lactic acid until estrus synchronization treatment is performed, with a fluctuation of vitamin A ranging from 5,000 IU to 50,000 IU per day, and t lactic acid ranging from 0.3 g to 5 g per day. Wherein the gilts in small-group are fed for 10 days and then transferred to breeding unit pens for feeding till an age of 209 d. A daily ration fed for group-housed gilts contains the vitamin A at a concentration of 1,700 IU/kg, and that for still-housed gilts is 4700 IU/kg. The gilts in the small-group are fed ad libitum, and an average daily feed intake of still-housed gilts is 2.2 kg; the pubertal gilts at age of 210 days are fed with 20 mg per day of altrenogest to achieve estrus synchronization for 18 consecutive days. Estrous detection is performed on the second day after the end of altrenogest. The gilts are artificially inseminated firstly at 8-16 h after the beginning of estrus, the second insemination is performed 24 h later.

Therefore, by utilizing the method in the present disclosure, it can alleviate the delayed puberty onset or estrus disorder of the gilts caused by insufficient estrogen synthesis, reduce the feeding duration and feeding cost for the gilts; and it also facilitate synchronous estrus, increase an estrus rate and a piglet index of the gilts, which has great values of promoting batch farrowing used in pig farms, achieving the goal of "all-in-all-out" and reducing costs and increasing efficiency in pig breeding industry.

Use of Vitamin a Combined with Lactic Acid in Preparation of Feed

In another aspect of the present disclosure, the present disclosure provides a use of vitamin A combined with lactic acid in the preparation of feed. According to the embodiments of the present disclosure, the feed is used for at least one of the following: the gilts housed in batch farrowing; promoting puberty onset of the gilts; increasing an estrus rate and a piglet index of the gilts; alleviating estrus disorder of the gilts; shortening feeding duration of the gilts before moved into batch; and promoting estrogen synthesis of the gilts.

According to the embodiments of the present disclosure, the vitamin A combined with lactic acid is applied prior to the puberty onset of the gilts. At this moment, the gilts are in a state of low estrogen level and are prone to have delayed puberty onset or estrus disorder. By feeding the vitamin A combined with lactic acid, it can effectively advance the puberty onset of the gilts, or alleviate the estrus disorder, thereby increasing the reproduction efficiency of the gilts, increasing the estrus rate and the piglet index of the gilts, and shortening the feeding duration of the gilts before moved into batch.

According to the embodiments of the present disclosure, the estrus disorder includes latent estrus or anestrus.

According to the embodiments of the present disclosure, the feed is used for facilitating Cyp19a1 gene expression in follicular granulosa cells. Therefore, it is helpful to promote the follicular development.

Solutions of the present disclosure will be explained below in combination with examples. Those skilled in the art will understand that, the examples below are merely used to illustrate the present disclosure, but should not be regarded as a limitation to the scope of the present disclosure. The examples without indicated specific technologies or conditions are conducted according to the technologies or conditions described in literatures in the art or according to the product instructions. The used reagents or instruments without indicated manufacturers are all commercially available conventional products.

Example 1. Use of Vitamin A Combined with Lactic Acid in Promoting Estrogen Synthesis in Granular Cells and Puberty Onset of Mice 1. Detection of Expression Change of a Key Enzyme for Lactic Acid Synthesis in Ovaries of Mice Before and After Puberty Onset The ovaries were separately isolated from pre-pubertal and post-pubertal female ICR mice, immobilized with 4% of PFA, then paraffin embedding was performed after dehydrated; the paraffin sectioning was stained with immunofluorescence staining to detect the protein expression of LDHA, a key enzyme in lactic acid synthesis. Results (FIG. 1) showed that the protein expression of the LDHA was increased in post-pubertal mice, which indicated that the lactic acid was useful for follicular development (a prerequisite for the increase of estrogen synthesis in granular cells in follicles). Thus, in subsequent examples, the combine vitamin A with lactic acid may promote the synthesis of estrogen.

2. In-Vitro Culture of Isolated Granular Cells of Mice

Figure 2A:
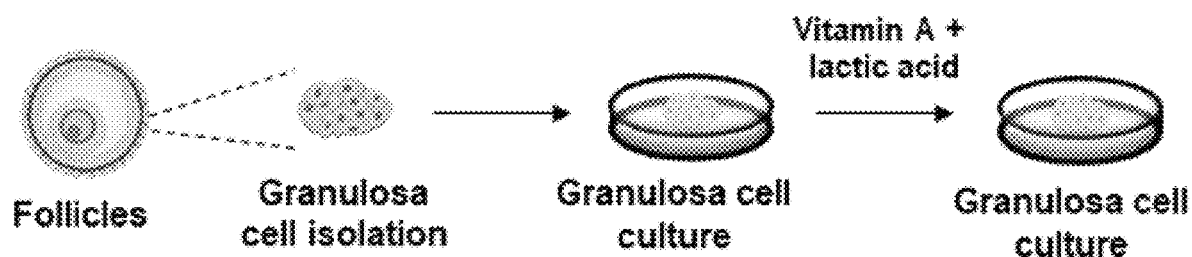
FIG. 2A to FIG. 2C shows an analysis diagram of vitamin A combined with lactic acid promoting the protein expressions of CYP19A1 of granular cells in mice, wherein FIG. 2A, a schematic diagram for isolation and culture of the granular cells of mice and the treatment with vitamin A combined with lactic acid.

As shown in FIG. 2A, 8-week-old adult mice were killed by cervical dislocation to collect the ovaries. The ovaries washed with sterile PBS were then transferred into a culture dish containing DMEM/F12 (without phenol red). The follicles were punctured by a hypodermic needle, and granular cells in follicles were released into the culture medium. The granular cells were selected under a stereoscope and the cumulus-oocytes complexes and ovarian tissues were discarded. Then, the granular cells were precipitated by centrifugation (5 minutes, 1500 rpm), washed with the PBS for 3 times, and then cultured in a 6-well plate with a DMEM/F12 culture medium containing 10% heat-inactivated foetal bovine serum, 100 U/mL penicillin and 50 mg/mL streptomycin. Each well contains $2\times10^6$ cells. The cells were cultured in an incubator with 5% $CO_2$ at 37° C. for 24 hours, then randomly divided into a control group and a treatment group (vitamin A combined with lactic acid). After 24 hours of pre-culture, the culture medium was replaced with a DMEM/F12 medium containing 2% heat-inactivated foetal bovine serum; and cultured in an incubator with 5% $CO_2$ for 24 hours respectively to collect the cells and the medium for further experimental analysis. Finally, western blotting of the protein CYP19A1 and an estradiol concentration were detected.

Figure 2B:
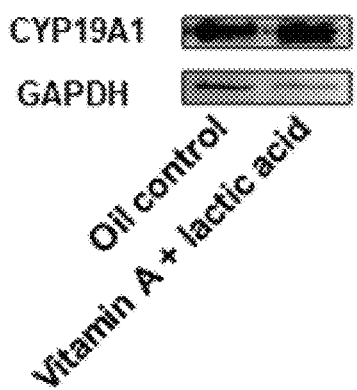
Figure 2C:
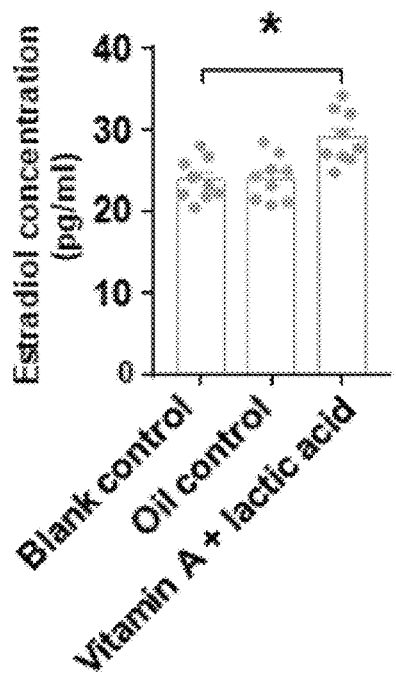

The results were shown as FIG. 2. It can be seen that, the vitamin A combined with the lactic acid significantly increased the protein expression level of the CYP19A1 in the granular cells (referring to FIG. 2B), and increased the concentration of the estradiol at the same time (referring to FIG. 2C).

Figure 3A:
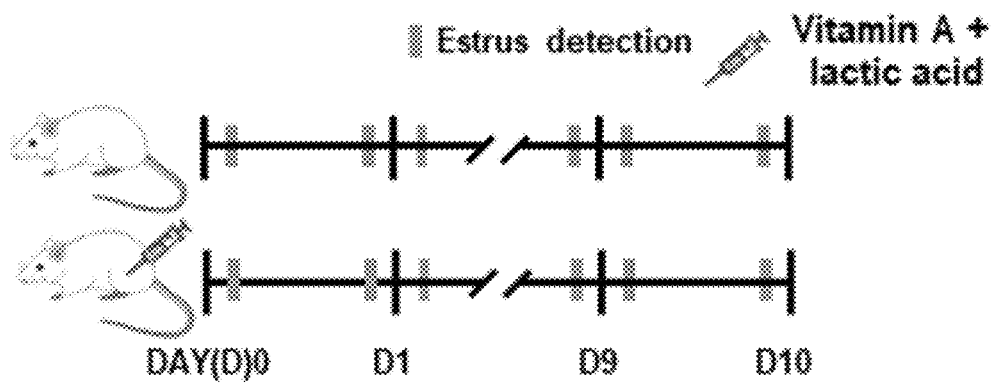
FIG. 3A and FIG. 3B show an analysis diagram of an effect of vitamin A combined with lactic acid on the onset of puberty of mice.

3. The 3-Week-Old Female Mice were Treated with Vitamin a Combined with Lactic Acid and the Estrus Initiation Time was Detected As shown in FIG. 3A, 3-week-old female ICR mice were injected with vitamin A combined with lactic acid compound preparation; and the ratio of vaginal opening and the onset of puberty in the mice were counted. A total of 30 normal weaned female ICR mice with an age of 3 weeks of 14 g were selected and divided into a control group and a treatment group (vitamin A combined with the lactic acid). The control group was injected with 0.05 mL of DMSO daily; and the vitamin A combined with the lactic acid injection group was injected with a 0.05 mL of DMSO solution containing 5 IU vitamins and 1 mg lactic acid daily. The vaginal opening was observed as follows: vaginal opening of the mice in each group were observed and recorded at 8 a.m. to 9 a.m. every day from the 24 days of age.

Figure 3B:
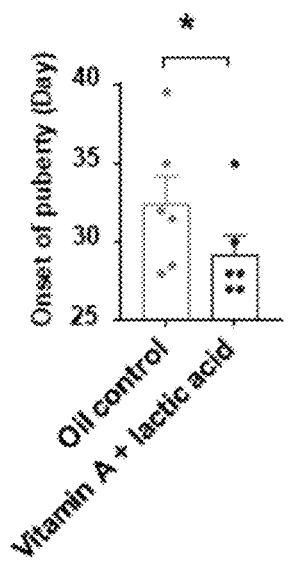

The results were shown as in FIG. 3B. The time of the vaginal opening in the mice could be advanced by using vitamin A combined with the lactic acid, and the onset of puberty in 3-week-old female ICR mice could be advanced by an average of 3.3 days.

Example 2. Use of Vitamin A Combined with Lactic Acid in Promoting the Puberty Onset of Gilts In the following embodiments, the reagents used were as follows:

Attractant: citric acid (0.3%), white sugar (0.3%), milk powder (2%); and the solvent is water.

Daily ration fed in small-group: the content of vitamin A was 1700 IU/Kg without lactic acid.

Daily ration fed in breeding unit pen: the content of vitamin A was 4700 IU/Kg without lactic acid.

1. Feed Induction in Gilts

All the gilts were crossbred of Landrace and Large White. To enable the gilts to adapt to subsequent feeding with the vitamin A combined with lactic acid, it is necessary to perform feed induction in advance. The feed induction lasted for 3 days at a frequency of once in the morning and once in the afternoon every day. The attractant was prepared in proportion by using a plastic basin; and the flavor of the attractant was adjusted to be sour and sweet; and then the attractant was sucked by a 10 mL oral syringe for feed induction. During feed induction, staff, firstly standing outside the fence, injected a small amount of attractant onto the railing to attract the gilts to eat. After entering the pen, the staff squat down and moved slowly to attract the gilts to intake the feed, and use mouth to imitate the sound of the gilts eating so as to form a conditioned reflex. When the gilts got close, the attractant was gently added to their mouths. The syringe should be appropriately raised to make the gilts develop the habit of raising their heads to eat, which could be ensure that the vitamin A combined with lactic acid would not spilled due to head lowering of the gilts during eating. For gilts that did not want to open mouth, feeding was not compulsory. After the gilts in one pigsty were fed, the gilts in next pigsty could be fed across the stalls so as to decrease stimulation to the gilts. Glits that had been successfully induced should be marked, and gilts that without successful induction for three days should be culled. The mouth opening rate of feed induction for gilts should be kept above 95%. After the feed induction was completed, the utensils such as oral syringe and plastic basin should be cleaned in time for next use.

2. Feeding Vitamin a Combined with Lactic Acid

In this test, the gilts were fed with the vitamin A combined with lactic acid from 140 d of age. The feeding duration was divided into two stages: gilts was housed in small group with feeding ad libitum; and then transferred to the breeding unit pens for feeding after 150 d of age. Those who feed vitamin A combined with lactic acid were consistent with those who performed feed induction; and the time of feeding vitamin A combined with lactic acid was set before feeding the daily ration in the afternoon daily, which was consistent with the time of feed induction.

The gilts that had been successfully induced were randomly divided into five groups: a control group, an oil control group, a low-dose group (12500 IU vitamin A+0.3 g lactic acid), a medium-dose group (25000 IU vitamin A+1.0 g lactic acid) and a high-dose group (50000 IU vitamin A+3.0 g lactic acid). No additional substance was supplemented in the control group; a total of 5 mL soybean oil was additionally fed per day in oil control group; and the three experimental groups were respectively fed 5 ml of soybean oil containing the different dose of vitamin A combined with lactic acid daily. The syringe should be appropriately raised to ensure gilts to raise their heads to completely swallow the oil. During housed in small-group, the gilts that had been fed needed to be marked by animal mark paint.

During the test, other test conditions of each group were completely consistent. The gilts housed in small group were fed ad libitum, and that housed in breeding unit pens were fed a fixed amount of feed at the fixed time, with an average daily feed intake of 2.2 kg/d. A daily ration fed for group-housed gilts contains the vitamin A at a concentration of 1,700 IU/kg, and that for still-housed gilts is 4700 IU/kg. The end of feeding gilts was set till the onset of puberty.

3. Estrus Detection

Estrus detection was performed from 150 d of age. Standing estrus reflex checking are used to detect estrus. When the sow has estrus and the back of the sow is pressed by hand, the sow will show standing reflex as well as red labia mucosa and increased thick secreting mucus, and the above performances could be used as basis for determining the estrus. At same time, purplish red-colored vulva, a large and thick of vaginal mucus are the indicators of estrus in gilts. The estrus detection was performed once every morning; the estrus time was recorded, and the backs of gilts in estrus were marked.

Figure 4:
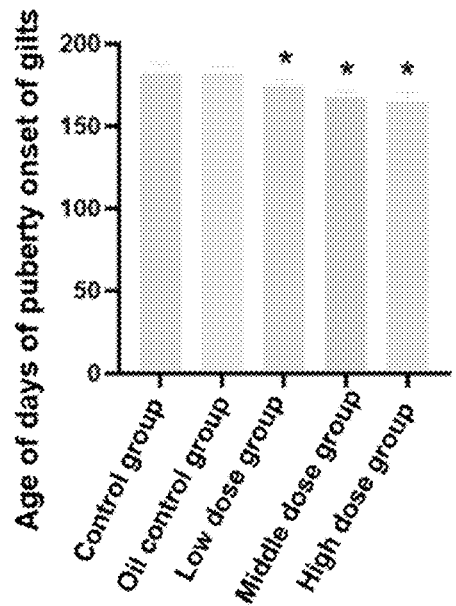
FIG. 4 shows an analysis diagram of an effect of vitamin A combined with lactic acid on the onset of puberty of gilts.

As shown in FIG. 4, the puberty onset of gilts can be effectively advanced by feeding with an appropriate amount of vitamin A combined with lactic acid. The puberty onset of gilts in low-dose group can be advanced by about 7.2 days; that in medium-dose group and in high-dose group respectively can be advanced by about 15 days and 17 days. It can be seen that, the onset of puberty for gilts can be significantly advanced by feeding with an appropriate amount of vitamin A combined with lactic acid. In this test, the vitamin A combined with lactic acid at different doses was used in different groups, including a low dose, a medium dose and a high dose. The results showed that, compared with control group, the onset of puberty was advanced in all experimental groups. The effect of advancing onset of puberty for gilts was gradually enhanced with the increasing dosage of vitamin A combined with lactic acid. The puberty onset of gilts in low-dose group could be advanced by about 7.2 days; that in medium-dose group and in high-dose group respectively can be advanced by about 15 days and 17 days. This result indicated that, vitamin A combined with lactic acid can improve reproductive performances of gilts in a dose-dependent manner, and make them enter estrus earlier, which has great significance for increasing the reproductive efficiency and production level of gilts. This also means that, in actual farming, a reasonable vitamin A combined with lactic acid may become an effective means of production management.

Figure 5:
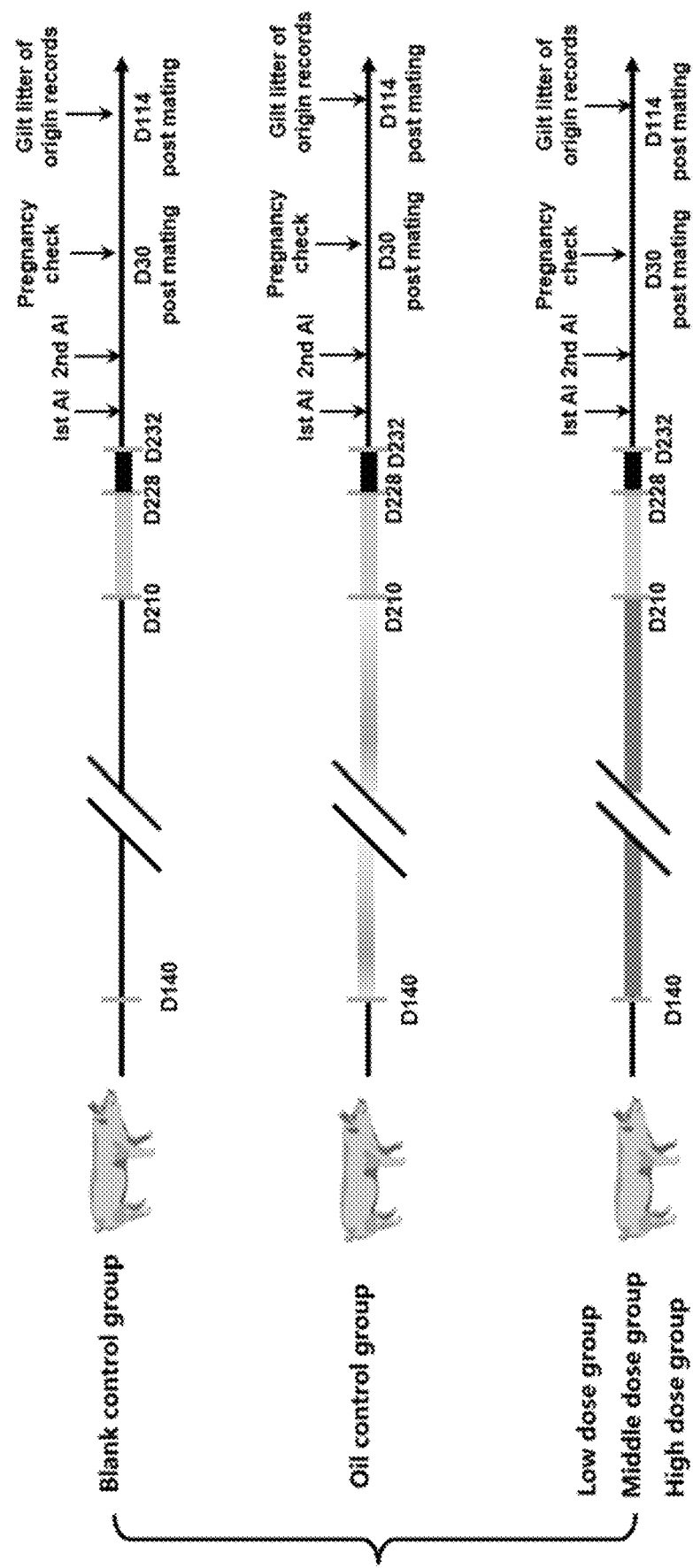
FIG. 5 shows a flow chart for the treatment of feeding the gilts with vitamin A combined with lactic acid to improve estrus disorder.

Example 3. Use of Vitamin A Combined with Lactic Acid in Improving Estrus Disorder and Increasing a Piglet Index of Gilts On the basis of example 2, gilts that have established estrus were performed with a timed-artificial insemination (referring to FIG. 5).

1. Feeding Combination of Vitamin a and Lactic Acid

In this test, the gilts were fed with the vitamin A combined with lactic acid from 140 d of age. The feeding duration was divided into two stages: gilts was housed in small group with feeding ad libitum; and then transferred to the breeding unit pens for feeding after 150 d of age. Those who feed vitamin A combined with lactic acid were consistent with those who performed feed induction; and the time of feeding vitamin A combined with lactic acid was set before feeding daily ration in the afternoon daily, which was consistent with the time of feed induction. The successful-induced gilts were randomly divided into five groups: a control group, an oil control group, a low-dose group (12500 IU vitamin A+0.3 g lactic acid), a medium-dose group (25000 IU vitamin A+1.0 g lactic acid) and a high-dose feeding group (50000 IU vitamin A+3.0 g lactic acid). No additional substance was supplemented in the control group; a total of 5 mL soybean oil was additionally fed per day in oil control group; and the three experimental groups were respectively fed 5 ml of soybean oil containing the different dose of vitamin A combined with lactic acid daily. The syringe should be appropriately raised to ensure the gilts to raise their heads to completely swallow the oil. During housed in small-group feeding, the gilts that had been fed needed to be marked by animal mark paint. During the test, other test conditions of each group were completely consistent. The gilts housed in small group pens were fed ad libitum, and that housed in breeding unit pens were fed a fixed amount of feed at the fixed time, with an average daily feed intake of 2.2 kg/d. A daily ration fed for group-housed gilts contains the vitamin A at a concentration of 1,700 IU/kg, and that for still-housed gilts is 4700 IU/kg. The end of feeding gilts was up to the age of 209 d.

2. Performing Timed-Artificial Insemination

The gilts were fed with 20 mg per day of altrenogest for 18 continuous days from an age of 210 d. Estrus detection for gilts were performed at the second day following the end of altrenogest, which lasted for 4 consecutive days with once in the morning and in the afternoon daily; The gilts that showed their first estrus were marked at the back, and then recorded; The first artificial insemination was conducted at an interval of 8 to 16 hours after estrous (when the estrus occurs in the morning, the artificial insemination was conducted in the afternoon; and when the estrus occurs in the afternoon, the artificial insemination is conducted in the next morning); and the second insemination was conducted at an interval of 24 hours later, with the first insemination time as mating time.

Figure 6:
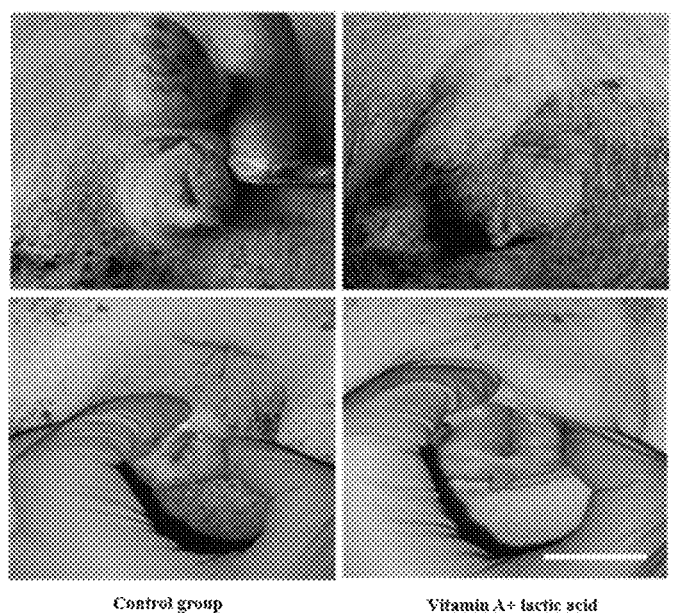
FIG. 6 shows an analysis diagram of an effect of feeding vitamin A combined with lactic acid on vulvar features of gilts during estrus.
Figure 7A:
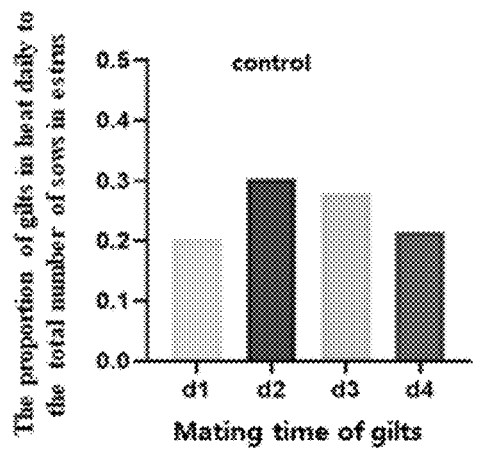
FIG. 7A to FIG. 7E show a diagram of an effect of vitamin A combined with lactic acid on the timing and concentration of estrus mating in gilts under the timed artificial insemination procedure.
Figure 7B:
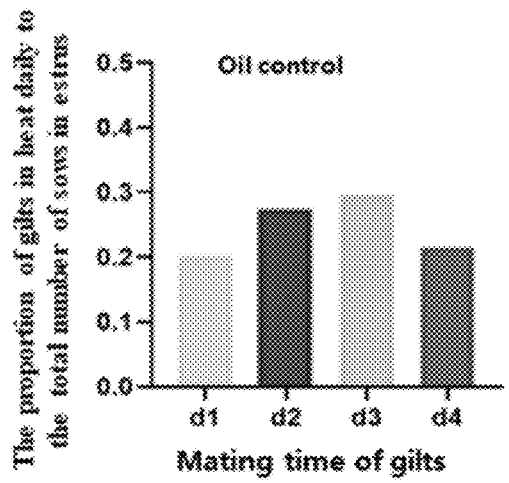
Figure 7C:
Figure 7D:
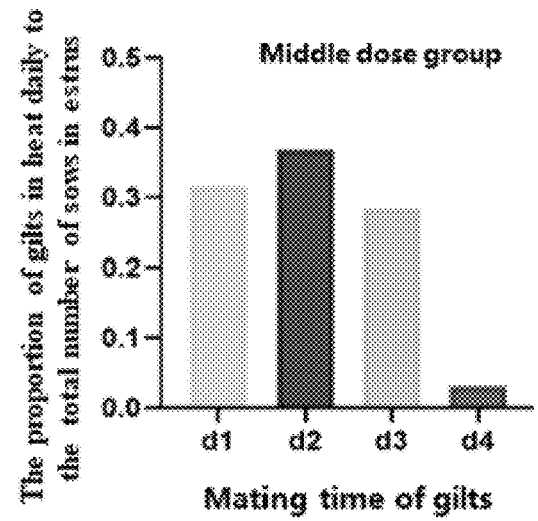
Figure 7E:
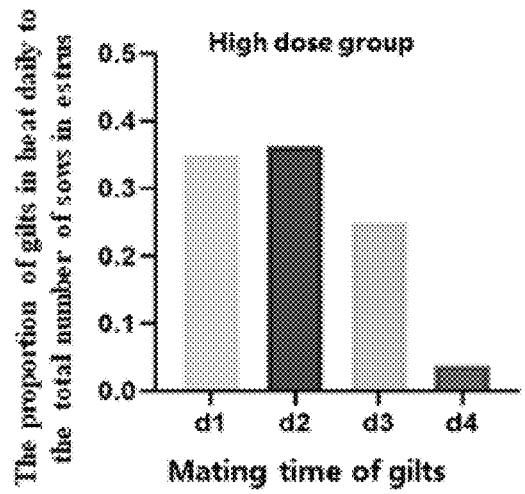

As shown in Table 1, the estrus rate and external estrus signs of gilts can be effectively increased by feeding an appropriate amount of the vitamin A combined with lactic acid. Compared with the control group, the estrus rate in low-dose group was increased by about 7.5%, and that in medium-dose group was increased by about 12%; the estrus rate in the high-dose group was increased by about 6%. It was further found that, the redness and swelling of the vulva of gilts in experimental groups was more obvious than that in the control group (FIG. 6).

In addition, as shown in FIG. 7A to FIG. 7E, it was found that the vitamin A combined with lactic acid could enable gilts to estrus earlier after altrenogest withdrawal, and increase the estrus concentration. The estrus of gilts in middle-dose group and high-dose group were mainly concentrated in the first three days after altrenogest withdrawal.

The litter birth of sows in each group was analyzed. The results were shown as Table 1. The litter born and the born health piglets of the sows in low-dose group were effectively increased. Meanwhile, the piglet index (PI) is a comprehensive index to measure the overall reproductive performance of the sow herd in current production, and refers to a number of live born piglets per 100 multiparous sows or gilts that are naturally mated or artificially inseminated. It can be seen from Table 1 that, not only the estrus detection rate, but also the piglet index, in low-dose group and medium-dose group, was also significantly higher than that in control group.

The traditional continuous-flow system has been difficult to adapt to high-speed development of pig industry. Further, since the whole pig market is facing severe challenges, a batch farrowing technology for sows has become an important measure for transformation and upgrading in pig farming. And the emergence of large-scale and batch farrowing will certainly bring a radical change to the pig industry. There are also some problems in the practical application of sow batch farrowing technology. However, the present disclosure provides an effective strategy for increasing estrus rate, reproduction efficiency and piglet index of the gilts in batch farrowing with fixed-time insemination; and a total of 160 live born piglets (weaned piglets) can be increased per 100 gilts. Therefore, the present disclosure will produce great economic and social value for promoting batch production.

TABLE 1

Statistical table for reproductive performances of the gilts

| Item | Control group | Oil control group | Low-dose group | Middle-dose group | High-dose group |
|---|---|---|---|---|---|
| Number of sample gilts | 110 | 105 | 100 | 120 | 103 |
| Number of -gilts having estrus | 83 | 84 | 83 | 105 | 84 |
| Estrus rate (%) | $75.45^b$ | $78^b$ | $83.00^{ab}$ | $87.50^a$ | $81.55^{ab}$ |
| Pregnancy rate of batch (%) | $72.73^b$ | $73.33^b$ | $82.00^{ab}$ | $85.83^a$ | $78.64^b$ |
| Farrowing rate (%) | $70.91^b$ | $72.38^b$ | $81.00^{ab}$ | $83.33^a$ | $77.67^b$ |
| Total number of piglets born per litter | $12.76 \pm 3.25^b$ | $12.78 \pm 3.44^b$ | $13.30 \pm 3.49^a$ | $12.99 \pm 3.32^b$ | $12.64 \pm 3.26^b$ |
| Number of piglets born alive per litter | $11.64 \pm 3.21^b$ | $11.77 \pm 3.46^b$ | $12.08 \pm 3.42^a$ | $12.15 \pm 3.67^b$ | $11.58 \pm 3.01^b$ |
| Piglet index | 842 | 863 | 978 | 1002 | 899 |

Notes:
(1) Pregnancy rate = number of gestation/number of the gilts taken × 100%;
(2) Farrowing rate = number of farrowing/number of the gilts taken × 100%;
(3) A calculation mode of the piglet index is: the average number litter size × farrowing rate × 100%;
(4) $^{a-d}$Different lowercase letters in the same column indicate significant differences between indicators (P < 0.05).

Although the embodiments of the present disclosure have been illustrated and described above, it may be understood that, the embodiments above are illustrative, and cannot be understood as a limitation to the present disclosure. Those skilled in the art can make changes, modifications, substitutions and variations to the above embodiments within the scope of the present disclosure.

What is claimed is:

1. A batch breeding method for gilts, comprising:
feeding, prior to puberty onset, the gilts with vitamin A combined with lactic acid; and
performing, subsequent to the puberty onset, estrus synchronization treatment and insemination treatment on the gilts,
wherein:
for each gilt, a feeding amount of the vitamin A ranges from 5,000 IU to 50,000 IU per day, and a feeding amount of the lactic acid ranges from 0.3 g to 5 g per day; and
the vitamin A combined with lactic acid is provided in the form of a mixture containing the vitamin A, the lactic acid and oil.

2. The method according to claim 1, wherein the gilts are fed with vitamin A combined with lactic acid every day from an age of 130 d to 150 d until the puberty onset or until the estrus synchronization treatment is performed.

3. The method according to claim 1, wherein said feeding gilts with vitamin A combined with lactic acid further comprises:
feeding the gilts in a small group for 8 days to 15 days, wherein a daily ration adopted during said feeding the gilts in the small group contains vitamin A at a concentration of 1,600 IU/kg to 1,800 IU/kg and contains no lactic acid; and
feeding the gilts in breeding unit pens for 20 to 50 days until the onset of puberty or the estrus synchronization treatment is performed, wherein a daily ration adopted during said feeding the gilts in breeding unit pens contains vitamin A at a concentration of 4,600 IU/kg to 4,800 IU/kg and contains no lactic acid.

4. The method according to claim 1, further comprising, prior to said feeding the gilts with vitamin A combined with lactic acid: performing a feed induction treatment on the gilts in advance, wherein:

a time of feed induction treatment to adapt to the subsequent vitamin A combined with lactic acid is 2 days to 4 days; and
the feed induction treatment comprises feeding the gilts with an attractant once in the morning and once in the afternoon every day.

5. The method according to claim 4, wherein:
said feeding the gilts with vitamin A combined with lactic acid is performed in the afternoon every day; and
a time of feeding the gilts with vitamin A combined with lactic acid is consistent with the time of feed induction treatment.

6. The method according to claim 1, wherein:
the estrus synchronization treatment comprises feeding gilts with 15 mg to 25 mg of altrenogest for 15 days to 20 days per day;
subsequent to the completion of the estrus synchronization treatment, timed-artificial insemination treatment or fixed-time artificial insemination treatment are performed on the gilts;
the timed-artificial insemination treatment comprises:
performing estrus detection on the gilts, and
performing insemination on the gilts subsequent to the appearance of estrus representation; and
the fixed-time artificial insemination treatment comprises:
applying exogenous gonadotropins and ovulation induction to the gilts for facilitating synchronization of follicular development and ovulation; and
performing fixed-time insemination on the gilts.

7. A feeding method for gilts in batch farrowing, comprising:
feeding gilts with vitamin A combined with lactic acid from an age of 140 days until estrus synchronization treatment is performed, a total of the vitamin A ranging from 5,000 IU to 50,000 IU per day, and a total of the lactic acid ranging from 0.3 g to 5 g per day, wherein the gilts are fed in a small group for 10 days, and then transferred to breeding unit pens and fed till an age of 209 d, a daily ration for gilts fed in the small group contains vitamin A at a concentration of 1,700 IU/kg, and a daily ration for gilts fed in breeding unit pens is 4700 IU/kg, the gilts housed in the small group are fed ad libitum, and an average daily feed intake of still-housed gilts is 2.2 kg;

feeding, from an age of 210 days, the pubertal gilts with altrenogest for 18 consecutive days to achieve estrus synchronization, wherein the altrenogest is fed by 20 mg per day;

performing, from the second day following the end of altrenogest, an estrous detection on the gilts every day;

performing, subsequent to the appearance of estrus signs, first insemination at an interval of 8 hours to 16 hours; and performing second insemination at an interval of 24 hours later.

8. A method for promoting puberty onset of gilts, comprising:

feeding, prior to puberty onset, the gilts with vitamin A combined with lactic acid; and performing, subsequent to the puberty onset, estrus synchronization treatment and insemination treatment on the gilts, wherein:

for each gilt, a feeding amount of the vitamin A ranges from 5,000 IU to 50,000 IU per day, and a feeding amount of the lactic acid ranges from 0.3 g to 5 g per day; and the vitamin A combined with lactic acid is provided in the form of a mixture containing the vitamin A, the lactic acid and oil.

9. The method according to claim 8, wherein the gilts are fed with vitamin A combined with lactic acid every day from an age of 130 d to 150 d until the puberty onset or until the estrus synchronization treatment is performed.

10. The method according to claim 8, wherein said feeding gilts with vitamin A combined with lactic acid further comprises:

feeding the gilts in a small group for 8 days to 15 days, wherein a daily ration adopted during said feeding the gilts in the small group contains vitamin A at a concentration of 1,600 IU/kg to 1,800 IU/kg and contains no lactic acid; and feeding the gilts in breeding unit pens for 20 to 50 days until the onset of puberty or the estrus synchronization treatment is performed, wherein a daily ration adopted during said feeding the gilts in breeding unit pens contains vitamin A at a concentration of 4,600 IU/kg to 4,800 IU/kg and contains no lactic acid.

11. The method according to claim 8, further comprising, prior to said feeding the gilts with vitamin A combined with lactic acid: performing a feed induction treatment on the gilts in advance, wherein:

a time of feed induction treatment to adapt to the subsequent vitamin A combined with lactic acid is 2 days to 4 days; and the feed induction treatment comprises feeding the gilts with an attractant once in the morning and once in the afternoon every day.

12. The method according to claim 11, wherein:

said feeding the gilts with vitamin A combined with lactic acid is performed in the afternoon every day; and a time of feeding the gilts with vitamin A combined with lactic acid is consistent with the time of feed induction treatment.

13. The method according to claim 8, wherein:

the estrus synchronization treatment comprises feeding gilts with 15 mg to 25 mg of altrenogest for 15 days to 20 days per day;

subsequent to the completion of the estrus synchronization treatment, timed-artificial insemination treatment or fixed-time artificial insemination treatment are performed on the gilts;

the timed-artificial insemination treatment comprises:
performing estrus detection on the gilts, and
performing insemination on the gilts subsequent to the appearance of estrus representation; and the fixed-time artificial insemination treatment comprises:
applying exogenous gonadotropins and ovulation induction to the gilts for facilitating synchronization of follicular development and ovulation; and
performing fixed-time insemination on the gilts.

14. A method for alleviating estrus disorder of gilts, comprising:

feeding, prior to puberty onset, the gilts with vitamin A combined with lactic acid; and performing, subsequent to the puberty onset, estrus synchronization treatment and insemination treatment on the gilts, wherein:

for each gilt, a feeding amount of the vitamin A ranges from 5,000 IU to 50,000 IU per day, and a feeding amount of the lactic acid ranges from 0.3 g to 5 g per day; and the vitamin A combined with lactic acid is provided in the form of a mixture containing the vitamin A, the lactic acid and oil.

15. The method according to claim 14, wherein the gilts are fed with vitamin A combined with lactic acid every day from an age of 130 d to 150 d until the puberty onset or until the estrus synchronization treatment is performed.

16. The method according to claim 14, wherein said feeding gilts with vitamin A combined with lactic acid further comprises:

feeding the gilts in a small group for 8 days to 15 days, wherein a daily ration adopted during said feeding the gilts in the small group contains vitamin A at a concentration of 1,600 IU/kg to 1,800 IU/kg and contains no lactic acid; and feeding the gilts in breeding unit pens for 20 to 50 days until the onset of puberty or the estrus synchronization treatment is performed, wherein a daily ration adopted during said feeding the gilts in breeding unit pens contains vitamin A at a concentration of 4,600 IU/kg to 4,800 IU/kg and contains no lactic acid.

17. The method according to claim 14, further comprising, prior to said feeding the gilts with vitamin A combined with lactic acid: performing a feed induction treatment on the gilts in advance, wherein:

a time of feed induction treatment to adapt to the subsequent vitamin A combined with lactic acid is 2 days to 4 days; and the feed induction treatment comprises feeding the gilts with an attractant once in the morning and once in the afternoon every day.

18. The method according to claim 17, wherein:

said feeding the gilts with vitamin A combined with lactic acid is performed in the afternoon every day; and a time of feeding the gilts with vitamin A combined with lactic acid is consistent with the time of feed induction treatment.

19. The method according to claim 14, wherein:

the estrus synchronization treatment comprises feeding gilts with 15 mg to 25 mg of altrenogest for 15 days to 20 days per day;

subsequent to the completion of the estrus synchronization treatment, timed-artificial insemination treatment or fixed-time artificial insemination treatment are performed on the gilts;

the timed-artificial insemination treatment comprises:
  performing estrus detection on the gilts, and
  performing insemination on the gilts subsequent to the appearance of estrus representation; and the fixed-time artificial insemination treatment comprises:
  applying exogenous gonadotropins and ovulation induction to the gilts for facilitating synchronization of follicular development and ovulation; and
  performing fixed-time insemination on the gilts.

* * * * *